Feb. 22, 1949. H. C. SWIM Plant Pat. 828
ROSE PLANT
Filed June 17, 1947
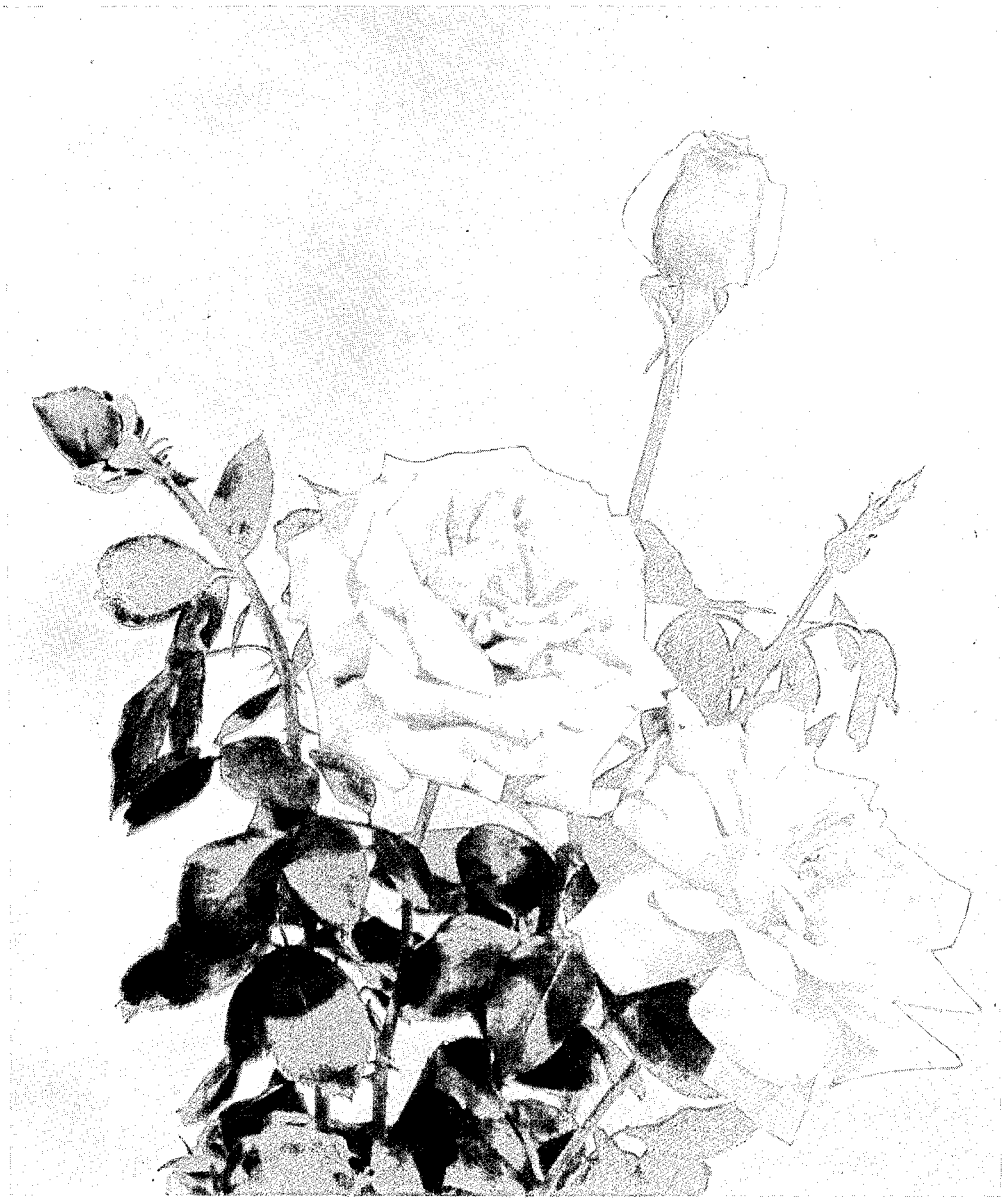
Inventor:
H. C. Swim
By: Robb & Robb
Attorneys.

Patented Feb. 22, 1949

Plant Pat. 828

UNITED STATES PATENT OFFICE

828

ROSE PLANT

Herbert C. Swim, Ontario, Calif., assignor to Armstrong Nurseries, Inc., Ontario, Calif., a corporation of California Application June 17, 1947, Serial No. 755,152

1 Claim. (Cl. 47—61)

The present invention relates to a new and distinct variety of rose plant originated by crossing of the variety "Charlotte Armstrong" (Pl. Pat. #445) and an unnamed red rose seedling (unidentified). This cross resulted in a new variety having a combination of distinctive characteristics which, as far as I am aware, are not to be found in any other rose known to commerce.

Referring to the novel features of this new rose, the color combination of the buds and flowers, together with the large size and number of petals is of primary importance—more petals and larger in size than ony other variety in the color range illustrated.

Secondly, the penetrating and pleasing fragrance is quite unusual and somewhat difficult to classify, but probably most commonly referred to as spicy.

Thirdly, the plant produces a normal amount of foliage with leaflets, both heavy and leathery, but having a high degree of resistance to rust, though with only a moderate degree of resistance to mildew.

Fourthly, the plant growth is very vigorous, bushy and upright. It produces moderately long stems of strong and fairly straight character with many large and many small thorns, and one of the unique characteristics is the unusual color of the stem on the side exposed to the sun, somewhat similar to only two other rose varieties, namely, "Betty Uprichard" (unpatented) and "Grande Duchesse Charlotte" (Plant Patent 774).

Asexual reproduction of this new variety shows the foregoing characteristics come true to form and are established.

In the drawings are shown specimens of the flowers and foliage in different stages of development, depicting the unique color combinations of said flowers at such stages.

The following is a detailed description of the new variety, color terminology being in accordance with Robert F. Wilson's Horticultural Colour Chart with exceptions noted from Ridgway's Color Standards and Nomenclature:

Type: Hardiness untested; bush; outdoor; seedling; for cut flowers and garden decoration.
Class: Hybrid tea.
Breeding: Seedling.
*Seed parent.*—"Charlotte Armstrong."
*Pollen parent.*—Unnamed red rose seedling.

Propagation: Holds its distinguishing characteristics through succeeding propagations by budding.

*Flower*

Locality where grown: Ontario, California.
Flowers borne: Singly, sometimes two and three, to stem; on strong, long stems.
Quantity of bloom: Abundant; outdoors.
Continuity: Continuous during growing season.
Fragrance: Penetrating; probably spicy.
Bud:
*Peduncle.* — Medium to long; medium heavy; erect; medium rough; numerous gland-tipped cilia and prickles. *Color*—between Kildare Green, Plate XXXI (Ridgway) and Absinthe Green, Plate XXXI (Ridgway).
*Before calyx breaks.* — *Size* — medium. *Form*—ovate with foliaceous appendages, gland-tipped cilia, glandular bloom, on the surface of the bud; with slender, much cut foliaceous parts extending beyond the tip of the bud equal to one-half or more of its length.
*As calyx breaks.*—*Color*—near Chrysanthemum Crimson, Plate 824/1, page 169. *Inner surface* — with fine, woolly tomentum; when the margin of a sepal is not covered by the margin of an adjacent sepal, it has woolly tomentum and stipitate glands on both margins; but if margin is covered with adjacent sepals, margin has only woolly tomentum.
*As first petal opens.*—*Size*—medium. *Form*—medium to long; urn. *Color*—outside—near Cardinal Red, Plate 822, page 168, shading through Cardinal Red, Plate 822/2, page 168, with very small blotch of Lemon Yellow, Plate 4/1, page 4, at base of petal. Inside—Crimson, Plate 22, page 22, shading through Crimson, Plate 22/1, page 22, with narrow margin of Crimson, Plate 22/2, page 22. Base of petal shading to near Cardinal Red, Plate 822/1, page 168, with small blotch of Indian Yellow, Plate 6/1, page 6, at base of petal.
*Openings*—Opens up well.
Bloom: Size, when fully open—Medium to large; 3¾'' to 4¼''.
*Petalage.*—Double; from 24 to 32 petals, 3 to 5 petaloids; arranged regularly.
*Form.*—High center at first; becoming open; petals remaining at first loosely rolled outward; becoming later, at maturity, tightly rolled outward.

3

Petals: Medium thick; leathery; with inside satiny and outside shiny.

*Shape.*—Outside: broadly obovate with apex notched with one notch; intermediate: obovate, cuneate, with apex notched with one notch; inside: obovate, cuneate, with apex notched with one notch.

*Color.*—Colors may be modified by being blotched and shaded with other colors.

This description of a newly opened flower was made from a rose grown outdoors in the month of September, at Ontario, California:

*Color.* — *Outside petal* — outside surface: Cardinal Red, Plate 822/3, page 168, shading to Rose Red, Plate 724/2, page 158, with small blotch of Lemon Yellow, Plate 4/2, page 4, at base of petal; inside surface: Crimson, Plate 22/1, page 22, shading to Crimson, Plate 22/2, page 22, with shading of Geranium Lake, Plate 20/1, page 20, near base of petal, with blotch of Lemon Yellow, Plate 4/1, page 4, at base of petal. *Intermediate petal* — outside surface: Crimson, Plate 22/1, page 22, shading to Crimson, Plate 22/2, page 22, with small blotch of Lemon Yellow, Plate 4/2, page 4, at base of petal; inside surface: Crimson, Plate 22/2, page 22, shading to Crimson, Plate 22/3, page 22, at margin. Base of petal with blotch of Lemon Yellow, Plate 4/2, page 4. *Inner petal*—outside surface: Crimson, Plate 22/1, page 22, shading to Crimson, Plate 22/2, page 22, with small blotch of Lemon Yellow, Plate 4/2, page 4, at base of petal; inside surface: Crimson, Plate 22/2, page 22, shading to Crimson, Plate 22/3, page 22, at margin. Base of petal with blotch of Lemon Yellow, Plate 4/2, page 4.

This description was made from a rose that was open for three days outdoors in the month of September, at Ontario, California:

*Color.* — *Outside petal* — outside surface: China Rose, Plate 024/1, page 111, shading to China Rose, Plate 024/2, page 111, with small blotch of Lemon Yellow, Plate 4/2, page 4, at base of petal; inside surface: Tyrian Rose, Plate 24/2, page 24, shading to Tyrian Rose, Plate 24/3, page 24, with a blotch of Lemon Yellow, Plate 4/1, page 4, at base of petal. *Inside petal*—outside surface: Between Phlox Pink, Plate 625, page 77, and Phlox Pink, Plate 625/1, page 77, with a blotch of Lemon Yellow, Plate 4/2, page 4, at base of petal; inside surface: Neyron Rose, Plate 623/2, page 76, shading to Neyron Rose, Plate 623/3, page 76, at outer edges with a blotch of Lemon Yellow, Plate 4/2, page 4, at base of petal.

*General color effect.*—Newly opened flower—Crimson, Plate 22/2, page 22. Three days open—Crimson, Plate 22/3, page 22.

*Behavior.*—Drop off cleanly; fading to a general color of Crimson, Plate 22/3, page 22, in hot weather.

*Flower longevity.*—On bush in garden—two to three days in September. Cut roses grown outdoors kept at living-room temperatures—two days in September.

*Reproductive organs*

Stamens: Medium number; arranged irregularly about pistils and mixed with petaloids.

4

Filaments: Medium to long; 5 to 12 mm. in length. *Color*—near Saturn Red, Plate 13/2, page 13, most with anthers.

Anthers: Medium size; all open at once approximately. *Color*—near Indian Yellow, Plate 6/2, page 6, with apex near Neyron Rose, Plate 623/1, page 76.

Pollen: Moderate. *Color*—near Yellow Ochre, Plate 07/1, page 101.

Pistils: Approximately 75 in number.

Styles: Uneven; medium length; medium to heavy; loosely bunched. *Color*—Blood Red, Plate 820/1, page 166, at upper end, gradually changing to Sap Green, Plate 62/3, page 62, at base.

Stigma: Grayish white, somewhat translucent.

Ovaries: Some protruding from calyx.

Hips: This variety very seldom sets seed under normal growing conditions.

Foliage:

*Leaves.*—Compound of five to seven leaflets; normal; medium size; heavy and leathery.

*Leaflets.*—Shape—oblong with apex acute. Base—obtuse. Margin—doubly serrate.

*Color.*—Mature—upper surface: near Cress Green, Plate XXXI (Ridgway); under surface: Deep Chrysolite Green, Plate XXXI (Ridgway) with veins near Light Cress Green, Plate XXXI (Ridgway). Young—Upper surface: near Kronberg's Green, Plate XXXI (Ridgway), margins washed with Deep Corinthian Red, Plate XXVII, (Ridgway); under surface: near Lime Green, Plate XXXI (Ridgway), washed with Deep Corinthian Red, Plate XXVII (Ridgway).

*Rachis.*—Medium heavy. Upper side—grooved; stipitate glands on edges; under side—moderately prickly and stipitate glands.

*Stipules.*—Medium long; medium wide; with medium points turning out at an angle of more than 45°, somewhat straight.

*Disease.*—Resistant to mildew.

Growth:

*Habit.*—Bushy; upright; much branched.

*Growth.*—Vigorous.

*Canes.*—Medium to heavy.

*Main stems.*—Near Dull Citrine, Plate XVI (Ridgway), becoming overlaid with Light Seal Brown, Plate XXXIX (Ridgway), and Bone Brown, Plate XL (Ridgway), on surfaces exposed to the sun.

*Large prickles.*—Many; medium length; hooked very slightly downward; with medium narrow base. *Color*—near Rood's Brown, Plate XXVIII (Ridgway), becoming Vandyke Brown, Plate XXVIII (Ridgway), at apex.

*Small prickles.*—Several. *Color*—near Rood's Brown, Plate XXVIII (Ridgway).

*Hairs.*—None.

*Branches.*—Light Cress Green, Plate XXXI (Ridgway). *Large prickles*—several; medium length; hooked very slightly downward; with short, narrow base. *Color*—near Sayal Brown, Plate XXIX (Ridgway). *Small prickles*—Many. *Color*—near Sayal Brown, Plate XXIX (Ridgway). *Hairs*—none.

*New shoots.*—Light Elm Green, Plate XVII (Ridgway), washed with Indian Red, Plate XXVII (Ridgway), on side exposed to sun. *Large prickles*—several; medium length; with short, narrow base. *Color*—near Vinaceous-Russet, Plate XXVIII (Ridgway). *Small prickles*—several. *Color*—near Vinaceous-Russet, Plate XXVIII (Ridgway). *Hairs*—none, but several stipitate glands.

For purposes of comparison, it may be noted that this new variety of rose resembles the well-known variety "Betty Uprichard" more than any other rose known to me, but it resembles this latter variety only with respect to the distinctive coloration of the canes and to a lesser extent the color of the buds and flowers. It differs from "Betty Uprichard" in all other respects, however, in that the flowers have an average number of petals approximately twice that of "Betty Uprichard." The coloring of the inner surfaces of the petals is of a more intense shade; the plants are more vigorous and floriferous and the stems have many more thorns than "Betty Uprichard." (While "Betty Uprichard" is generally classified as fragrant and is so described by the American Rose Society, it has been generally considered to be only very delicately fragrant at least in California, whereas this new variety has a penetrating fragrance which strongly scents a room in which cut flowers of the variety are placed.)

This new variety of rose is an anomaly in that it has practically no resemblance to either of its parents. About the only similarity to either parent is to be found in the quantity of the large and small thorns of this new variety which are similar to the quantity of the large and small thorns of its parent "Charlotte Armstrong." There is possibly a slight resemblance between this new variety and its parent "Charlotte Armstrong" in the habit of growth, although this new variety is more bushy and floriferous than "Charlotte Armstrong." While both this new variety and its pollen parent are fragrant kinds, the type is quite different because the pollen parent was characterized by a heavy damask fragrance, whereas this new variety has a fragrance that is more appropriately described by the term spicy. The color of this new variety has no resemblance to that of either parent since it has a distinct contrast between the color of the outside of the petals and that of the inside. Neither parent was characterized by the distinctive coloration of the stems of this new variety where they are exposed to the sun.

I claim:

A new and distinct variety of rose plant, characterized as to novelty by the color combination of the buds and flowers, size and petalage of said flowers, penetrating and pleasing fragrance of the flowers, high degree of resistance to rust of the foliage, vigorous, bushy and upright growth of the plant, moderately long, strong and straight stems with many large and small thorns, and the unusual color of the stems on the side exposed to the sun, substantially as shown and described.

HERBERT C. SWIM.

No references cited.